United States Patent
Katsuki et al.

(10) Patent No.: US 6,723,879 B2
(45) Date of Patent: Apr. 20, 2004

(54) PROCESS FOR PREPARING AMINO COMPOUNDS BY USING SALEN-MANGANESE COMPLEXES AS THE CATALYST

(75) Inventors: Tsutomu Katsuki, Fukuoka (JP); Yoshinori Kohmura, Okazaki (JP)

(73) Assignee: Japan Science and Technology Corporation, Saitama-Ken (JP)

( * ) Notice: Subject to any disclaimer, the term of this patent is extended or adjusted under 35 U.S.C. 154(b) by 0 days.

(21) Appl. No.: 10/275,634

(22) PCT Filed: Oct. 17, 2001

(86) PCT No.: PCT/JP01/09090

§ 371 (c)(1), (2), (4) Date: Nov. 7, 2002

(87) PCT Pub. No.: WO02/076932

PCT Pub. Date: Oct. 3, 2002

(65) Prior Publication Data

US 2003/0139627 A1 Jul. 24, 2003

(30) Foreign Application Priority Data

Mar. 26, 2001 (JP) ......................................... 2001-086653

(51) Int. Cl.⁷ ..................... C07C 303/40; C07C 311/20; B01J 31/22

(52) U.S. Cl. ........................ 564/408; 564/445; 564/462

(58) Field of Search ................................. 564/408, 445, 564/462

(56) References Cited

PUBLICATIONS

Database CAPLUS on STN, Acc. No. 1992:214263, O'Conner et al., Tetrahedron Letters (1992), 33(8), p. 1001–1004 (abstract).*
Database CAPLUS on STN, Acc. No. 1994:77102, Noda et al., Synlett (1993), 7, p. 469–471 (abstract).*
Tetrahedron Letters, (1996), 37(51), p. 9245–9248.*
Tetrahedron, (1999), 55(49), p. 13937–13946.*

* cited by examiner

*Primary Examiner*—Brian Davis
(74) *Attorney, Agent, or Firm*—Fay, Sharpe, Fagan, Minnich & McKee, LLP

(57) ABSTRACT

Disclosed is a process for the enantioselective production of an optically active amino compound by the amination of the C—H bond of an organic compound. The amino compound is produced by converting the C—H bond at the allyl position of an alkene or the C—H bond at the benzyl position of an alkylarene to the corresponding C—N bond, using a salen-manganese complex as the catalyst and N-substituted iminoaryliodinane as the amination agent. Both the catalytic activity and the enantioselectivity are very high when there is used a catalyst in which the 3- and 5-positions of the salicylaldehyde moiety of the salen ligand are substituted with an electron-withdrawing group, particularly with a halogen atom.

6 Claims, 1 Drawing Sheet

PROCESS FOR PREPARING AMINO COMPOUNDS BY USING SALEN-MANGANESE COMPLEXES AS THE CATALYST

TECHNICAL FIELD

The present invention relates to a novel process for producing amino compounds, and particularly to a process for producing amino compounds by enantioselectively converting C—H bonds at the allyl positions of alkenes or at the benzyl positions of aklylarenes, to the corresponding C—N bonds.

PRIOR ART

The amination of C—H bonds of organic compounds is one of the most useful techniques in synthetic chemistry, particularly because a number of compounds having amino groups exhibit physiological activities that make them important as medicinal or agricultural materials and their intermediates.

However, reactions applicable to the amination of C—H bonds are actually very few. Only a small number of amination reactions have been proposed for the C—H amination using complexes of metals with porphyrin, cyclic amines or bipyridine as catalysts. Another such reaction is the one proposed by the present inventors, in which the amination reaction of C—H bonds proceeds under Kharash-Sosnovsky conditions using a copper catalyst (Japanese Patent Application Publication No. 140044/1998). However, these reactions are all directed to the preparation of simple amino compounds and none are for producing optically active aminocompounds. While some asymmetric syntheses have been proposed for preparing optically active compounds through the amination of C—H bonds using metal complexes as catalysts, the enantioselectivities are low, generally on the order of 20 to 30% at most.

It is a primary object of the present invention to provide a new process for the amination of C—H bonds of organic compounds, particularly to provide a process by which optically active amino compounds can be produced in an enantioselective manner by the amination of the C—H bonds.

DISCLOSURE OF THE INVENTION

After extensive studies the present inventors have now discovered that the utilization of specific salen-metal complexes as catalysts enables a highly enantioselective amination of C—H bonds at allyl positions of alkenes or at benzyl positions of alkylarenes and established a new process that achieves the above-mentioned object.

Thus, according to the present invention there is provided a process for producing an amino compound from an alkene or from an alkylarene, which comprises converting the C—H bond at the allyl position of the alkene or the C—H bond at the benzyl position of the alkylarene, to the C—N bond, wherein there are used an optically active salen-manganese complex as the catalyst and a N-substituted iminoaryliodinane as the amination agent.

In a preferred embodiment of the present invention, the optically active salen-manganese complex is one expressed by formula (1):

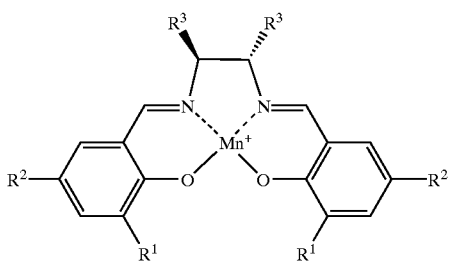

In the formula (1), at least one of $R^1$ and $R^2$ denotes an electron-withdrawing group, and $R^3$ denotes an alkyl group, having 1 to 4 carbon atoms or phenyl group, which may be a substituted one, or the two $R^3$'s are linked together to form a five- to seven-membered alicyclic hydrocarbon group.

In a more preferred embodiment of the present invention, the electron-withdrawing group is a halogen atom, preferably bromine, and the amination agent is N-(p-toluenesulfonyl) iminophenyliodinane.

BEST MODE FOR CARRYING OUT THE INVENTION

Figure 1:
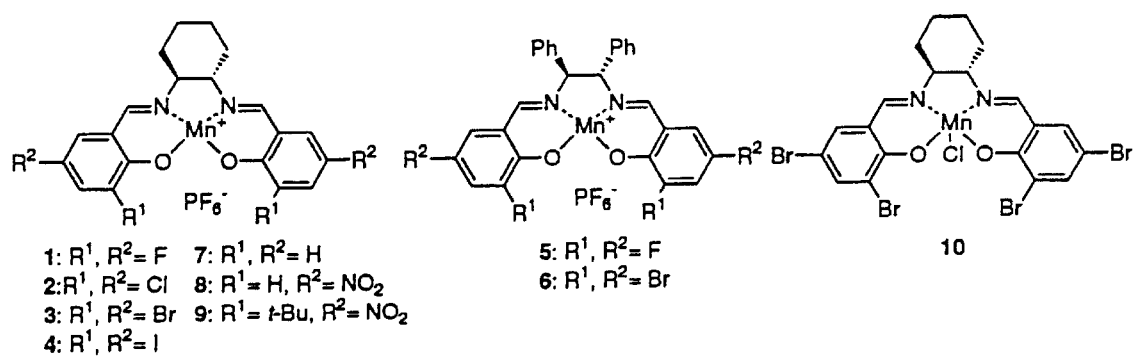
FIG. 1 shows examples of salen-manganese complexes used as the catalysts in the present invention.

Although it has been known that salen-metal complexes, particularly salen-manganese complexes, serve as catalysts for aziridination reaction, no attempt has ever been made to utilize them as catalyst for the amination reaction of C—H bond. The present invention is the first example of asymmetric C—H amination using salen-manganese complexes.

A salen-metal complex is a complex composed of a metal coordinated with a salen ligand, and it is well known that a salen ligand is a ligand of Bis-Schiff base type formed by the dehydrocondensation reaction of a salicylaldehyde compound with an ethylenediamine compound. By an optically active salen-manganese complex used in the present invention is meant a complex in which a salen ligand of chiral molecular structure coordinates with manganese (III). While generally such optically active salen-manganese complexes may exhibit catalytic activities for the amination of C—H bonds, preferred complexes are those expressed by formula (1):

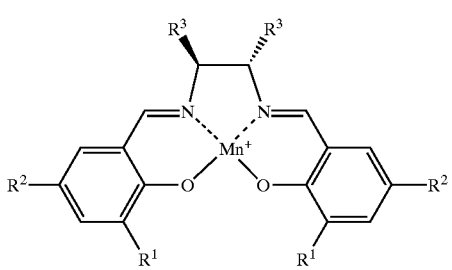

In the formula (1), at least one of $R^1$ and $R^2$ denotes an electron-withdrawing group. Thus, the catalytic activity is enhanced where the 3-position (3'-position) and/or 5-position (5'-position) of the salicylaldehyde moiety of the salen complex is substituted with an electron-withdrawing group, preferably with a halogen atom. Bromine-substituted complexes are most preferable because they exhibit an extremely high catalytic activity and enantioselectivity. $R^1$ or $R^2$ that is not an electron-withdrawing group generally denotes a hydrogen atom (that is, not substituted). $R^3$ denotes an alkyl group, having 1 to 4 carbon atoms or phenyl group, which may be a substituted one. Otherwise, the two $R^3$'s are linked together to form a five- to seven-membered alicyclic hydrocarbon group. A particularly preferred salen-manganese complex is one expressed by the following formula (1'), in which the two $R^3$'s are linked together to form a six-membered alicyclic hydrocarbon, cyclohexane, in the formula (1):

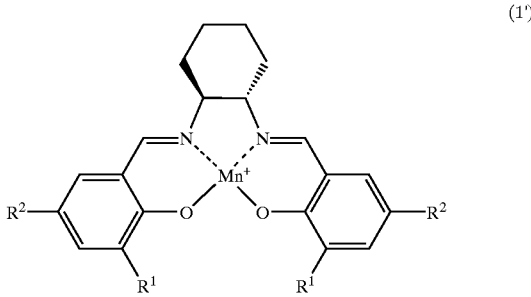

(1')

According to the present invention, amino compounds can be produced from alkenes or alkylarenes using the above-defined salen-manganese complexes as catalysts. The amination agent used in the invention is an N-substituted iminoaryliodinane and thus can be expressed by formula (2):

(2)

In the formula (2), Ary denotes an aryl group and R is selected from the functional or atomic groups expressed by formulae (3)–(5):

(3)

(4)

(5)

In the formulae (3)–(5), R' denotes an alkyl group, generally having 1 to 6 carbon atoms, or phenyl group in which the phenyl groups may be substituted with an appropriate substituent such as a lower alkyl group having 1 to 6 carbon atoms. An example of particularly preferred N-substituted iminoaryliodinane as the amination agent is N-(p-toluenesulfonyl) iminophenyliodinane ($CH_3C_6H_4SO_2N$=IPh; hereinafter this is sometimes expressed by TsN=IPh).

The present invention is directed to the conversion of the C—H bonds at the allyl position of the alkenes or the C—H bonds at the benzyl position of alkylarenes, to the corresponding C—N bonds, using the above-mentioned N-substituted iminoaryliodinane as the amination agent. Thus, the present invention can be expressed in terms of a process for producing an amino compound which comprises reacting a N-substituted iminoaryliodinane as expressed by the above-mentioned formula (2) with a compound expressed by formula (6) below, using an optically active salen-manganese complex expressed by the above-mentioned formula (1) as the catalyst, so as to produce an amino compound expressed by formula (7):

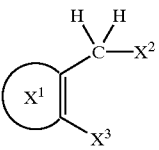

(6)

In the formula (6), $X^1$ may or may not be present and when present denotes an aromatic ring that may be a substituted one. In the case where $X^1$ is the aromatic ring, then the formula (6) expresses an alkylarene (an aralkyl compound). The aromatic ring is generally a benzene ring, but it may be another type of aromatic ring, e.g. a naphthalene ring. Such aromatic ring may be one substituted with appropriate substituent(s), for example, with alkyl group(s) having 1 to 6 carbon atoms, alkoxyl group(s) having 2 to 7 carbon atoms, alkylcarbonyloxy group(s) having 2 to 7 carbon atoms, alkoxycarbonyl group(s) having 2 to 7 carbon atoms, nitro group(s), cyano group(s), or halogen atom(s). In the case where $X^1$ is not present, then the formula (6) expresses an alkene.

In the formula (6), $X^2$ and $X^3$ each denotes independently hydrogen atom or an alkyl group having 1 to 6 carbon atoms, or otherwise X2 and X3 are linked together to form a five- to seven-membered alicyclic hydrocarbon group. Such alicyclic hydrocarbon may be one substituted with appropriate substituent(s), for example, with alkyl group(s) having 1 to 6 carbon atoms. In the case where $X^1$ is not present and furthermore $X^2$ and $X^3$ are linked together to form the alicyclic hydrocarbon group, then the formula (6) expresses a cycloalkene (a cyclic olefin).

The amino compound, the product produced by the present invention, can be expressed by formula (7):

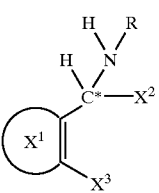

(7)

In the formula (7), R is the same as defined previously with respect to the formula (2), and $X^1$, $X^2$ and $X^3$ are respectively the same as defined previously with respect to the formula (6). Thus, according to the present invention, it is possible to convert the C—H bond at the allyl position of an alkene or at the benzyl position of an alkylarene to the corresponding C—N bond, by inserting a substituted nitrogen atom (NR) between the carbon atom and hydrogen atom forming such C—H bond. The protecting group (R) present in N-substituted iminoaryliodinane may be eliminated if necessary. It is to be noted that the aminated carbon atom is an asymmetric one, as shown in the formula (7), which means the present invention makes it possible to produce an optically active amino compound.

The amination reaction of the present invention as described in the above is generally carried out in an appropriate organic solvent (typically a chlorine-based solvent) at a temperature of −40° C. to room temperature for a period of one to fifty hours. Under the optimal condition where a salen-manganese complex is used as the catalyst, the enantioselectivity can reach as high as approx. 40 to 90% in terms of ee (enatiomer excess).

EXAMPLE

The invention will now be illustrated by the following examples, which are not for restricting the invention.

Example 1

Amination of Indan

The amination was carried out for the C—H bond at the benzyl position of indan as the starting material, in accordance with reaction formula (8):

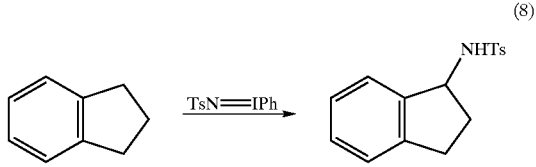

(8)

The salen-manganese complexes used as the catalyst are shown in FIG. 1. The amount of catalyst used was 6 mol %. The amination agent was (p-toluenesulfonyl) iminophenyliodinane and the reaction was carried out in $CH_2Cl_2$ solvent at a reaction temperature of 5° C. in the presence of a molecular sieve (MS-4A) as the dehydrating agent. The results are shown Table 1.

TABLE 1

| Run No. | Complex (catalyst) | Reaction Time(h) | Yield (%)[a] | ee (%)[b] | Optical Isomer[c] |
|---|---|---|---|---|---|
| 1 | 1 | 3 | 37 | 5 | S |
| 2 | 2 | 3 | 59 | 41 | S |
| 3 | 3 | 3 | 63 | 44 | S |
| 4 | ent-3 | 3 | 70 | 43 | R |
| 5 | 4 | 3 | 44 | 26 | S |
| 6 | 5 | 3 | 54 | 5 | S |
| 7 | 6 | 3 | 58 | 3 | S |
| 8 | ent-7 | 3 | 18 | 6 | R |
| 9 | 8 | 3 | 32 | 16 | S |
| 10 | 9 | 3 | 25 | 4 | S |
| 11 | 10 | 3 | 12 | 23 | S |

[a] Calculated from the quantity of TsN=IPh used.
[b] By HPLC analysis (DAICEL CHIRALPAK AD, hexane:2-propanol = 9:1)
[c] Determined from the order of elution of the product with p-toluenesulfonylated (R)-(-)-1-aminoindan in the HPLC analysis (cf. b).

As can be seen from Table 1, the catalytic activity was relatively low (Run No. 8) where there was used a salen-manganese complex in which the positions of $R^1$ and $R^2$ were not substituted (ent-7). In the case where a salen-manganese complex was used in which the positions of $R^1$ and $R^2$ were substituted with a halogen atom, an electron-withdrawing atom, both the catalytic activity and the enantioselectivity were enhanced (Run Nos. 1 through 5), with bromine atom being particularly preferable (Run Nos. 3 and 4).

The complex No. 3 and its enantiomer (ent-3) exhibited a similar level but reverse direction of enantioselectivity, demonstrating that such salen-manganese complexes as used in the present invention serve as an asymmetric catalyst. It can further be seen that the enantioselectivities in the C—H amination (Run Nos. 6 and 7), where there were used salen-manganese complexes containing a diphenylene moiety as the salen ligand (the complex Nos. 5 and 6), were low as compared with those where there were used the corresponding salen-manganese complexes containing a cyclohexanediamine (the complex Nos. 1 and 3). While catalytic activities were observed with salen-manganese complexes (the complex Nos. 8 and 9) in which the position of $R^2$ was substituted with a nitro group, the enantioselectivities were moderate (Run Nos. 9 and 10).

It appears that the introduction of a bulky substituent such as t-butyl group will lower the enantioselectivity (Run No. 10). It can also be seen that the use of neutral salen-manganese complex No. 10 as the catalyst, in place of the corresponding cationic salen-manganese complex No. 3, lowered both the catalytic activity and enantioselectivity (Run No. 11).

Example 2

Study on Solvent and Reaction Temperature

The amination reaction of indan was carried out in a similar manner as in Example 1, with varying types of solvent and reaction temperature, by using salen-manganese complex No. 3 as shown in FIG. 1 as the catalyst. The results are shown in Table 2.

TABLE 2

| Run No. | Solvent | Reaction Temperature (° C.) | Reaction Time (h) | Yield (%)[a] | ee (%)[b] | Optical Isomer[c] |
|---|---|---|---|---|---|---|
| 1 | $CH_2Cl_2$ | 5 | 3 | 63 | 44 | S |
| 2 | $CH_3CN$ | 5 | 3 | 0 | — | — |
| 3 | $CH_3CO_2C_2H_5$ | 5 | 3 | 19 | 32 | S |
| 4 | $CH_3COCH_3$ | 5 | 3 | 17 | 36 | S |
| 5 | $C_6H_5CH_3$ | 5 | 3 | 9 | 42 | S |
| 6 | $C_6H_5Cl$ | 5 | 3 | 62 | 47 | S |
| 7 | $CHCl_3$ | 5 | 3 | 62 | 47 | S |
| 8 | $(CH_2Cl)_2$ | 5 | 3 | 57 | 44 | S |
| 9 | $(CHCl_2)_2$ | 5 | 3 | 74 | 54 | S |
| 10 | $(CHCl_2)_2$ | −20 | 12 | 72 | 61 | S |
| 11 | $(CHCl_2)_2$ | −40 | 24 | 63 | 66 | S |

[a], [b], and [c] The same as in Table 1

As can be seen from in Table 2, the reaction was slow where acetonitrile, ethyl acetate, acetone or toluene was used as the solvent (Run Nos. 2 through 5). In general the reaction proceeded smoothly in the case where a halogen-containing solvent was used (Run Nos. 1, and 6 through 9), and the best result was obtained for the yield and the enantioselectivity when 1,1,2,2-tetrachloroethane was used as the catalyst (Run No. 9). The lowering of the reaction temperature resulted in an improvement in the enantioselectivity without decrease in the yield (Run Nos. 9 through 11), where the best enantioselectivity reached as high as 66% of ee at −40° C.

Example 3

Aminations of Various Compounds

The amination reaction was carried out with cyclohexene, tetralin, 1,1-dimethyltetralin or 1,1-dimethylindane as the starting alkene or alkylarene. The catalyst was salen-manganese complex No. 3 as shown in FIG. 1. The reaction was conducted for 24 hours at −40° C. using 1,1,2,2-tetrachlorethane as the solvent. The results are shown in Table 3.

TABLE 3

| Run No. | Substrate | Product | Yield(%)[a] | ee(%) |
|---|---|---|---|---|
| 1 | cyclohexene | cyclohexenyl-NHTs | 44 | 67[b] |
| 2 | cycloheptene | cycloheptenyl-NHTs | 42[c] | 41[b] |
| 3 | tetralin | 1-NHTs-tetralin | 67 | 77[d] |
| 4 | 1,1-dimethyltetralin | 1-NHTs-4,4-dimethyltetralin | 44 | 82[e] |
| 5 | 1,1-dimethylindan | 1-NHTs-3,3-dimethylindan | 71 | 89[f] |

[a] Calculated from the quantity of TsN=IPh used.
[b] By HPCL analysis (DAICEL CHIRALPAK AD, hexane:ethanol = 9:1).
[c] Analysis by $^1$H NMR showed that a small amount of aziridine was produced.
[d] By HPLC analysis (DAICEL CHIRALPAK AD, hexane:2-propanol = 9:1).
[e] By HPLC analysis (DAICEL CHIRALPAK AD, hexane:ethanol = 19:1).
[f] By HPLC analysis (DAICEL CHIRALPAK AD, hexane:2-propanol = 40:1).

In the case of cyclohexene, 1-[N-(p-toluenesulfonyl) amino] cyclohex-2-ene was produced with an ee of 67% and no aziridine derivative was detected. In the amination of cycloheptene, 1-[N-(p-toluenesulfonyl) amino] cyclohept-2-en was produced with an ee of 41% together with a small amount of aziridine derivative (the aminated product: the aziridinated product=4.8:1). The amination reactions at the benzyl positions of tetralin and 1,1-dimethyltetralin were good, with an enantioselectivity of 77% and ee of 82%, respectively. The enantioselectivity of 1,1-dimethylindan was outstandingly high: ee of 89%.

INDUSTRIAL APPLICABILITY

As described, the present invention enables the enantioselective production of optically active amino compounds from organic compounds using salen-manganese complexes as the catalyst.

What is claimed is:

1. A process for producing an amino compound from an alkene or from an alkylarene, which comprises converting the C—H bond at the allyl position of the alkene or the C—H bond at the benzyl position of the alkylarene, to the C—N bond, wherein there are used an optically active salen-manganese complex as the catalyst and a N-substituted iminoaryliodinane as the amination agent, the optically active salen-manganese complex being expressed by formula (1):

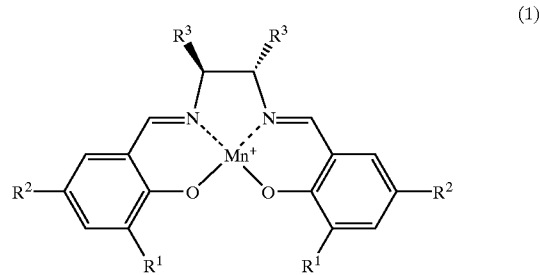

(1)

in which at least one of $R^1$ and $R^2$ denotes an electron-withdrawing group, and $R^3$ denotes an alkyl group having 1 to 4 carbon atoms, a phenyl group, or a group in which the two $R^3$'s are linked together to form a five- to seven-membered alicyclic hydrocarbon group.

2. The process for producing an amino compound as claimed in claim 1, wherein the electro-withdrawing group is a halogen atom.

3. The process for producing an amino compound as claimed in claim 2, wherein the halogen atom is bromine.

4. The process for producing an amino compound as claimed in claim 1, wherein N-(p-toluenesulfonyl) iminophenyliodinane is used as the amination agent.

5. The process for producing an amino compound as claimed in claim 2, wherein N-(p-toluenesulfonyl) iminophenyliodinane is used as the amination agent.

6. The process for producing an amino compound as claimed in claim 3, wherein N-(p-toluenesulfonyl) iminophenyliodinane is used as the amination agent.

* * * * *